(12) United States Patent
Lohrengel et al.

(10) Patent No.: US 7,044,133 B2
(45) Date of Patent: May 16, 2006

(54) FOLDED MEDICAL COVER FOR USE IN OPERATION ROOMS AND METHOD FOR FOLDING SAID COVER

(75) Inventors: Armin Lohrengel, Steinheim (DE); Theresia Knecht, Aalen (DE); Ralf Sprick, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 320 days.

(21) Appl. No.: 10/250,948

(22) PCT Filed: Jan. 18, 2002

(86) PCT No.: PCT/EP02/00476

§ 371 (c)(1),
(2), (4) Date: Jul. 9, 2003

(87) PCT Pub. No.: WO02/056786

PCT Pub. Date: Jul. 25, 2002

(65) Prior Publication Data
US 2004/0035334 A1    Feb. 26, 2004

(30) Foreign Application Priority Data
Jan. 18, 2001   (DE) .............................. 101 02 001

(51) Int. Cl.
*A61B 19/08*   (2006.01)

(52) U.S. Cl. ........................................ 128/851; 128/849
(58) Field of Classification Search ................ 128/849, 128/851

See application file for complete search history.

(56) References Cited

U.S. PATENT DOCUMENTS

| 3,747,655 A | 7/1973 | Hadtke |
| 5,379,703 A | 1/1995 | Marshall |

FOREIGN PATENT DOCUMENTS

| DE | 30 10 488 | 9/1981 |
| DE | 90 04 301 | 6/1991 |
| DE | 42 05 988 | 9/1993 |
| DE | 195 06 046 | 1/1996 |
| DE | 298 07 487 | 7/1998 |
| EP | 0 290 738 | 11/1988 |
| EP | 0 788 777 | 8/1997 |

Primary Examiner—Henry Bennett
Assistant Examiner—Camtu Nguyen
(74) Attorney, Agent, or Firm—Paul Vincent (57) ABSTRACT

The invention relates to a folded medical cover (30) for use in operation rooms, especially for instrument tables (2) or operation tables or for the extremities of a patient. The cover comprises a tubular section (36) with at least one first open end (32) for putting the cover onto the table (2) or the extremity, and has a second, preferably closed end (34). The tubular section (36) is folded at least once transverse to its longitudinal direction (16) and the second end (34) functions as a stop (53) when the cover is pulled over the table or the extremity. The aim of the invention is to simplify handling of such a cover. Towards this end, an intermediate section (46, 48), disposed in the longitudinal direction (16) between an end section (38, 40) forming the second end (34) and the first open end (32) is turned inwards into the tubular section (36) in such a manner that the table (2) or the extremity can be inserted in the opening (49, 86) formed by the inwardly turned intermediate section (46, 48) and that, when the cover (30) is put on the table (2) or the extremity, the intermediate section (46, 48) which is turned inward can be unfolded when the table (2) or the extremity rests against the second end (34) as the cover is being drawn on.

7 Claims, 7 Drawing Sheets

FOLDED MEDICAL COVER FOR USE IN OPERATION ROOMS AND METHOD FOR FOLDING SAID COVER

This application is the national stage of PCT/EP02/00476 filed on Jan. 18, 2002 and also claims Paris Convention priority of DE 101 02 001.5 filed on Jan. 18, 2001.

BACKGROUND OF THE INVENTION

The invention concerns a medical cover, preferably folded in a flat configuration, for use in an operation room, in particular for instrument tables or operation tables or extremities of a patient, comprising a tubular section with at least one open end for pulling onto the table or the extremity and comprising a second, in particular, closed end, wherein the tubular section is folded at least once transverse to a longitudinal direction, and wherein the second end forms a stop when pulling the cover onto the table or the extremity.

Instrument table covers of the above-described type for pulling onto or over an instrument table are known and described e.g. in U.S. Pat. No. 3,738,405, EP 0 290 738 B1, U.S. Pat. No. 3,747,655, DE 195 06 046 C1 and U.S. Pat. No. 5,379,703.

In the instrument table covers described in EP 0 290 738 B1 and U.S. Pat. No. 5,379,703, a relatively long tubular web which is substantially rolled, is folded in one or several layers on one side of the web (described below with reference to prior art shown in FIGS. 1 and 2). These known instrument table covers folded in this fashion, are disadvantageous in various ways. During pulling onto or over or reversely drawing over an instrument table, the table is introduced into the open end of the tubular web of the instrument table cover or, in other words, the instrument table cover is reversely drawn with its open end over the likewise substantially flat table top of the instrument table. In this procedure, when the table end reaches the first fold, the user experiences a resistance which is difficult to overcome in practice. In most cases, the user must secure the instrument table from rolling away with one foot or another assistant must hold the instrument table. In order to overcome the resistance of the initial fold, an assistant must normally lift the portion which is located above the first web section already pulled onto the instrument table and fold or roll it once or several times to allow the user to push the cover further onto the instrument table. This, however, can result in contamination of the cover. If no assistant is available, the second end of the folded configuration frequently falls down to contact the floor and the entire table cover must then be discarded.

Figure 2:
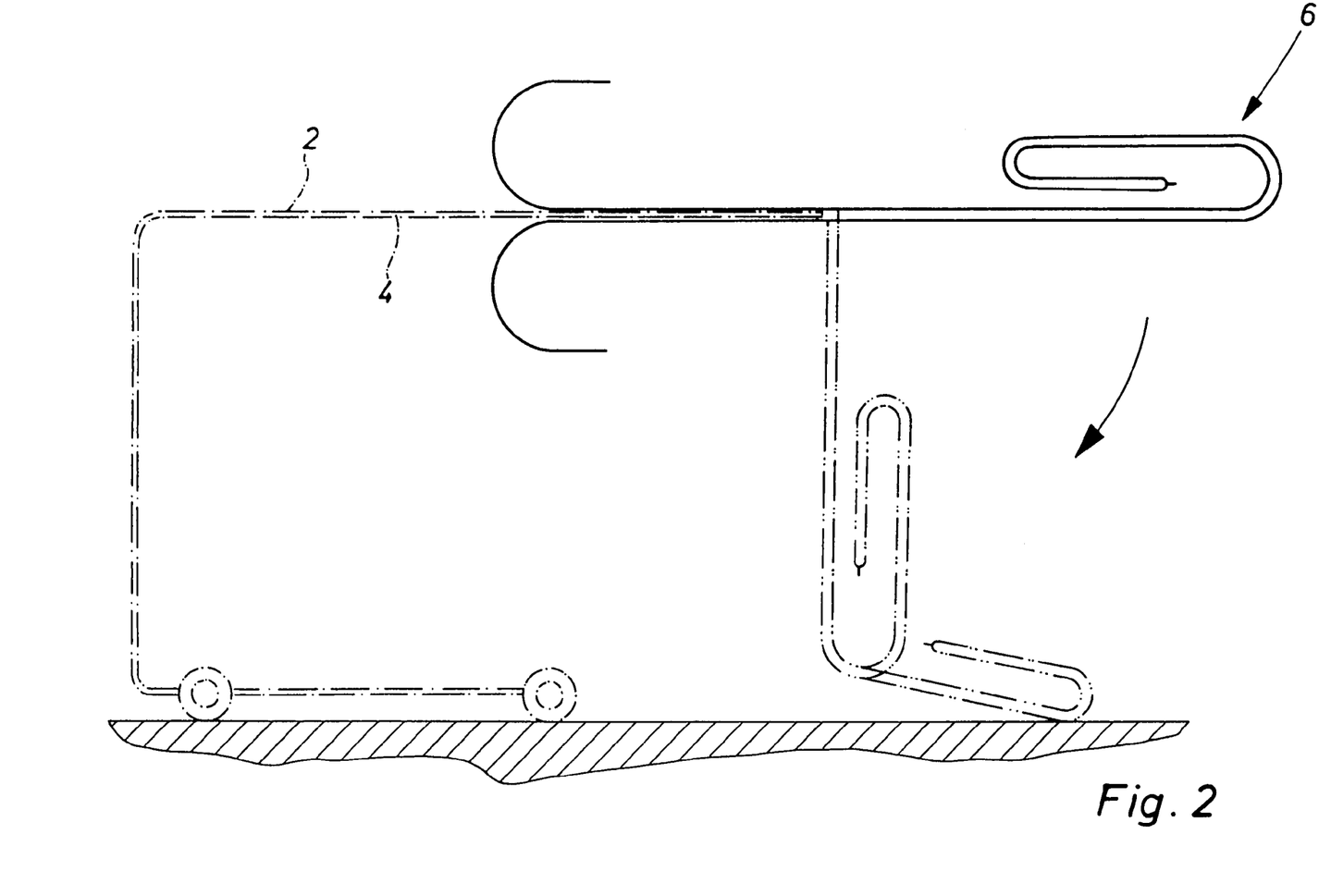
FIG. 2 also schematically shows the instrument table cover of FIG. 1 folded in a known manner, at a later point in time when being pulled onto an instrument table.

U.S. Pat. No. 3,747,655 solves the problem of uncontrolled unfolding or unrolling of the folded configuration by folding the cover in a zig-zag-like manner towards the outside (FIG. 2 of this US-document). The respective cover folds form a number of outwardly exposed, stepped folds which are disadvantageous since the gaps and folds can collect dirt or germs. Handling is more difficult since the user often does not grasp into the outermost fold, which forms a handling aid, with his/her hands, rather in a more inwardly disposed fold. When the cover is pulled onto an instrument table, the user strokes his/her hands over the surface of the cover or must repeatedly grasp the cover to unfold it, which is also disadvantageous with regard to contamination. The larger the number of outward folds in the tubular web, the closer they abut making it more difficult to correctly grasp and handle the cover when it is pulled onto the instrument table.

In view of the above, it is the underlying purpose of the present invention to improve a cover of the above-described type such that its handling is facilitated and the above-mentioned further disadvantages of conventional covers are largely eliminated.

SUMMARY OF THE INVENTION

This object is achieved in accordance with the invention with a cover of this type in that an intermediate section, which is disposed in the longitudinal direction between an end section forming the second end and the first open end, is reversely drawn into the tubular structure such that the table or the extremity can be introduced into the opening formed by the reversely drawn intermediate section and the reversely drawn intermediate section can be unfolded when the cover is pulled onto the table or the extremity when the table or the extremity abuts the second end during the covering procedure.

In accordance with the inventive solution, at least one intermediate section is reversely drawn or folded into the inside of the tubular web such that a section of the cover forming the outer visible side forms a bag-like receptacle for the remaining cover, wherein the folds, which represent an additional undesired increased risk of contamination of the cover and which can cause improper handling, are not visible from the outside. The reversely drawn or folded intermediate section prevents the cover from being unfolded or unrolled in an undesired and uncontrolled fashion when it is pulled onto an instrument table as is often the case for the above-mentioned conventional folds when tugged to overcome the resistance of a cover fold. Moreover, the resistance occurring when the table end abuts the usually closed end of the cover and the cover is pulled onto an instrument table, operation table or an extremity, e.g. the leg of a patient, has advantageously turned out to be low. The cover is unfolded with nearly no resistance and can be easily pulled over or reversely drawn onto the instrument table or a leg of a patient.

A handling aid can also be advantageously disposed in the region of the first open end for grasping the cover with one hand when pulling it onto the table or the extremity. This handling aid or handling aid means could be formed in any fashion, e.g. using tabs or similar engagement or holding means disposed on an outer side of the tubular web. However, embodiments are preferred with which the handling aid is formed by an edge section of the cover which either protrudes in the longitudinal direction to form a grasping region or which is outwardly folded to form a fold for engagement by the hand of the user. Folding of this edge section about the entire periphery keeps the folded cover in a preferably flatly folded configuration. In this case, the edge section preferably has a longitudinal extent of 0.2 to 0.5 times the length of the folded configuration.

To obtain sufficient overall extended length with minimum length of the folded configuration, it is advantageous to dispose several intermediate sections between the end section forming the second end and the first open end and reversely draw them inwardly into the tubular structure. To obtain a minimum length of the folded configuration, it is advantageous when the unfolding end formed by the reversely drawn intermediate section is proximate to the stop at the second end of the cover inside the tubular structure. The same also applies for the starting point of the reversely drawn intermediate section which should be at least approximately in the region of the first open end for optimized length.

The stop at the second end of the cover which should prevent the cover from being pushed too far onto the table or the extremity could be formed in any fashion, e.g. by tabs or strips on an otherwise open second end against which the free end of the table abuts thereby defining its end position. It is advantageous to form this stop by completely closing the second end e.g. by transverse welding of the tubular web.

At least one side of the cover has an absorbing surface, preferably comprising a fleece material.

The invention moreover concerns a method for folding a medical cover of the present type which is characterized by the method steps of independent claim 10.

In accordance therewith, the cover is made from a tubular web section e.g. by producing and supplying an endless tubular web which is separated into individual longitudinal sections before or after the inventive folding. The tubular web section may thereby be substantially oriented in a folding plane and forms an upper and a lower web with respective longitudinal ends and respective end sections. In accordance with the invention, an intermediate section which is disposed, in the longitudinal direction, between the end section forming the second end and the first open end, is folded inwardly into the tubular structure such that the intermediate section forms an opening for introducing the table or the extremity.

This produces a configuration which is folded in accordance with the invention. When the cover is pulled onto an instrument table, the table top is introduced into the opening formed and delimited by the intermediate section folded into the inside of the tubular structure.

When the configuration is flatly folded, an upper and a lower part of the intermediate section abut. For some applications, a separating layer or the like, which is not part of the cover, may optionally be disposed between the upper and lower parts of the intermediate section.

In a method variant according to claim 12, a tubular web section, in particular having two open ends, is pulled onto a first tubular body such that it projects past that tubular body. The intermediate section is then reversely drawn into the tubular structure by means of a second tubular body of slightly smaller diameter than the first and starting from the projecting part of the tubular web section, by pushing the second tubular body into the first tubular body and carrying along the intermediate section.

In accordance with the method variant of claim 13, the part of the tubular section projecting past the first tubular body forms the intermediate section. When the intermediate section is reversely drawn, the tubular section does not slide relative to the first tubular body. Method variants are also feasible and advantageous with which the projecting part of the tubular section is grasped by the second tubular body and reversely drawn into it thereby dragging the section to slide over the first tubular body.

The second tubular body can also advantageously be guided radially inwardly when it is pushed into the first tubular body. This can be effected by any guiding means, e.g. a third tubular body. The first tubular body itself preferably forms the guiding means.

An end stop may also be provided which delimits insertion of the second tubular body and which may advantageously be formed by a collar on the second tubular body which extends radially outwardly or by a stop means on the first tubular body, which extends radially inwardly.

As mentioned above, the stop may be produced, in particular after reversely drawing in the intermediate section, preferably by closing the second end of the tubular structure, e.g. by welding or gluing.

It is also advantageous to outwardly fold an edge section in the region of the first open end after folding and reversely drawing in the intermediate section.

Further features, details and advantages of the invention can be extracted from the drawing and the following description of a prior art and an inventive embodiment of the cover.

DESCRIPTION OF THE PREFERRED EMBODIMENT

Figure 1:
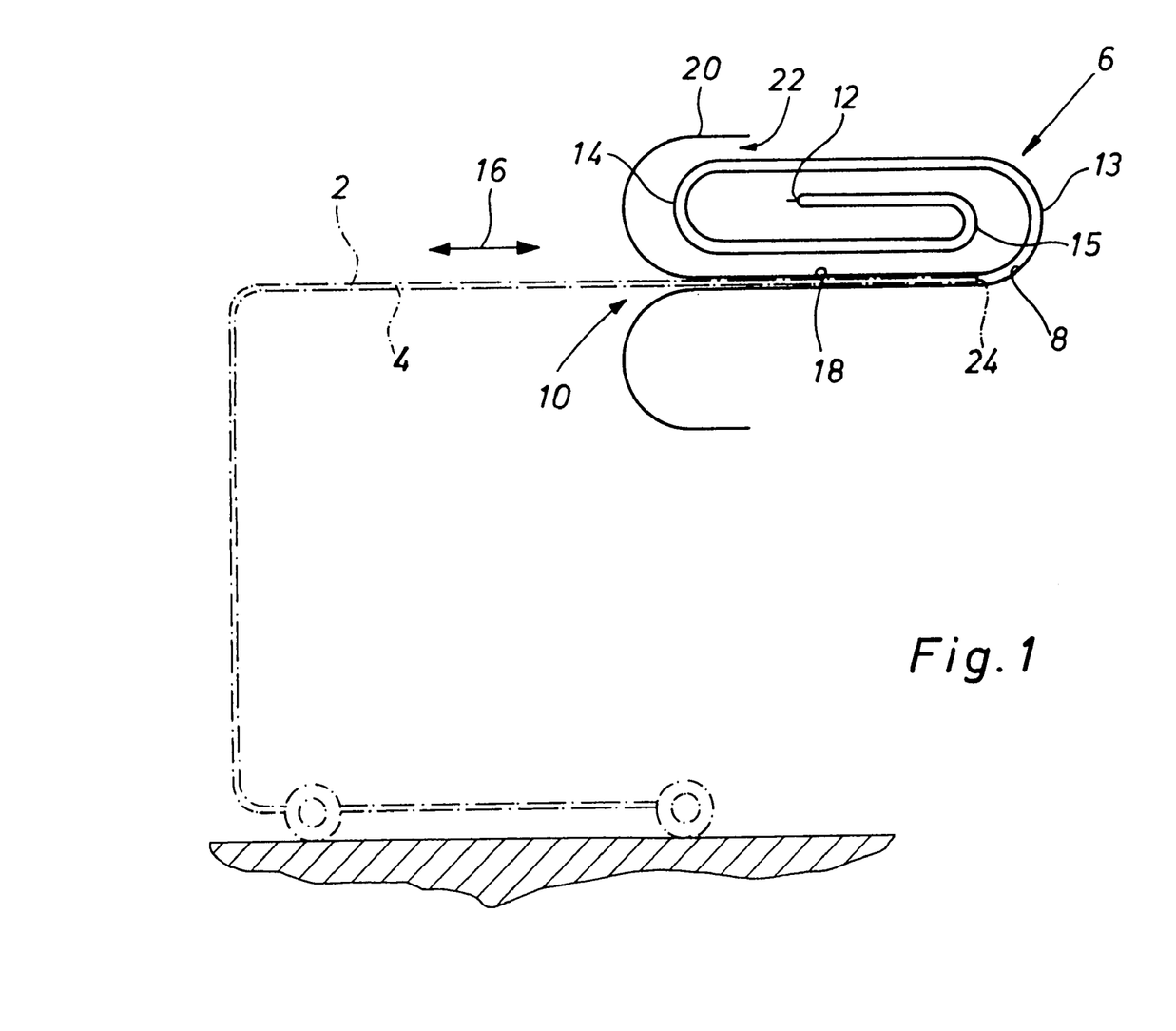
FIG. 1 schematically shows a conventional instrument table cover being pulled onto an instrument table.

FIG. 1 schematically shows an instrument table 2 comprising a planar table top 4 and an instrument table cover 6 folded in accordance with prior art. The instrument table cover 6 comprises a tubular web section 8 which is shown in FIG. 1 in a section perpendicular to the folding plane of the cover. The tubular web section 8 has a first open end 10 and a second closed end 12 and is folded up between the open end 10 and the closed end 12 in three folds (reference numerals 13, 14, 15), which are transverse to the longitudinal direction 16, wherein the overall folded configuration rests on a first upper side 18 of the tubular web section 8.

For application of the instrument table cover 6, the user hands grasp a pocket 22 formed by an outwardly folded edge section 20. He/she then pulls the folded cover 6, with its open end 10, over the free end 24 of the table top 4 of the instrument table 2. As indicated in FIG. 1, the free end 24 abuts the first fold 13 thereby producing undesired resistance which is very difficult to overcome in practice. Since the instrument table 2 usually has rollers, it tends to move back and may have to be held by an additional person. The instrument table cover 6 is then often unrolled or unfolded in an undefined fashion (shown schematically in FIG. 2) with the risk that the other end falls down and contacts the floor (indicated in FIG. 2) before the cover can be further pulled onto the instrument table top 4.

Figure 3:
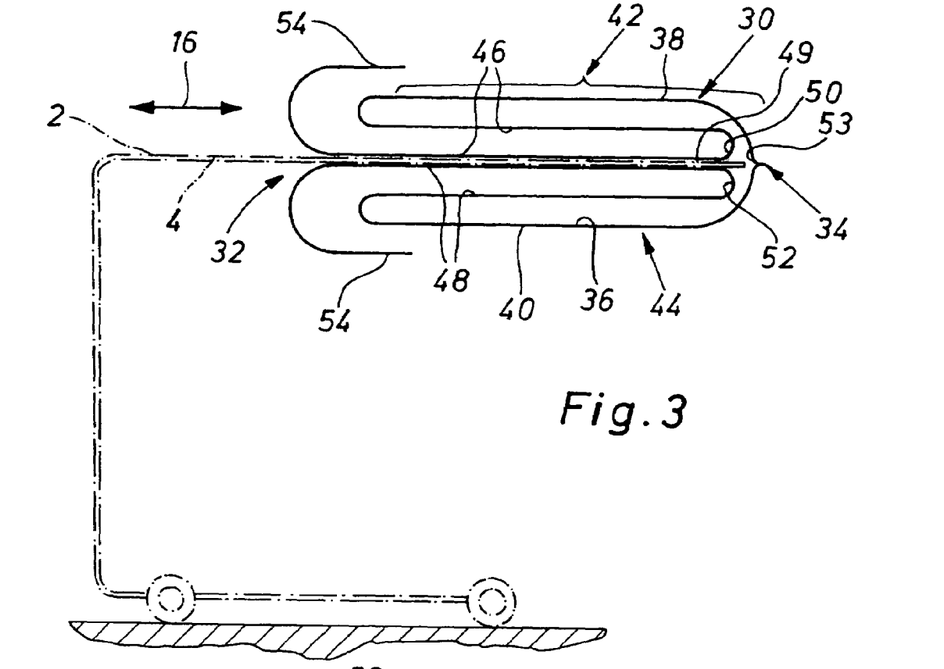
FIG. 3 schematically shows an embodiment of the instrument table cover folded in accordance with the invention, being pulled onto an instrument table.

FIG. 3 schematically shows an embodiment of a cover 30 for an instrument table 2, operation table or an extremity of a patient which is folded in accordance with the invention. Similar to the known cover, the cover 30 folded in accordance with the invention has a first open end 32 and a second end 34 which is closed in the embodiment shown. The cover 30 is also produced from a tubular web section 36 which has, in its flatly folded configuration, a first upper web section 38 and a second lower web section 40, relative to a folding plane which extends perpendicular to the plane of the drawing of FIG. 3

The first and second web sections 38, 40 have respective end sections 42, 44 which form the second end 34 and also the outer visible sides of the cover in the embodiment shown in FIG. 3. The first and second web sections 38, 40 each have an intermediate section 46, 48 disposed between the respective end section 42, 44 and the open end 32. These intermediate sections 46, 48 are reversely drawn or folded into the tubular structure 36 in the longitudinal direction 16 to such an extent that an unfolding end 50, 52 thereby formed is proximate to the inside of the second closed end 34 of the cover 30. If the cover is not flatly folded as shown in FIG. 3, but e.g. tubular, the intermediate sections 46, 48 join to form a substantially cylindrical opening 49 for receiving the table.

Figure 4:
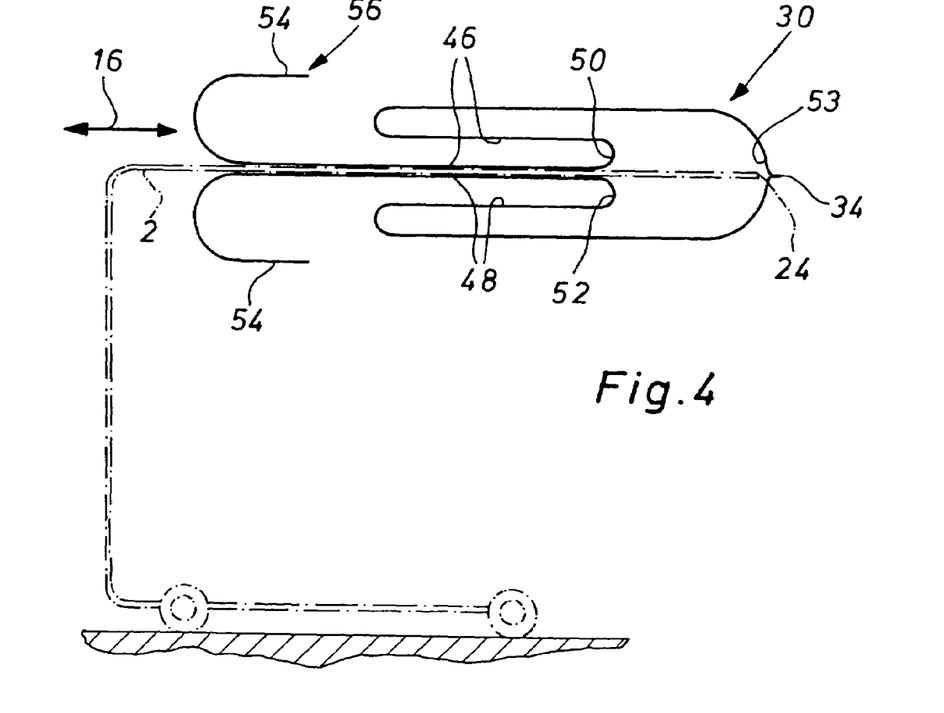
FIG. 4 schematically shows the instrument table cover in accordance with FIG. 3 folded in accordance with the invention being pulled onto an instrument table at a later point in time.
Figure 5:
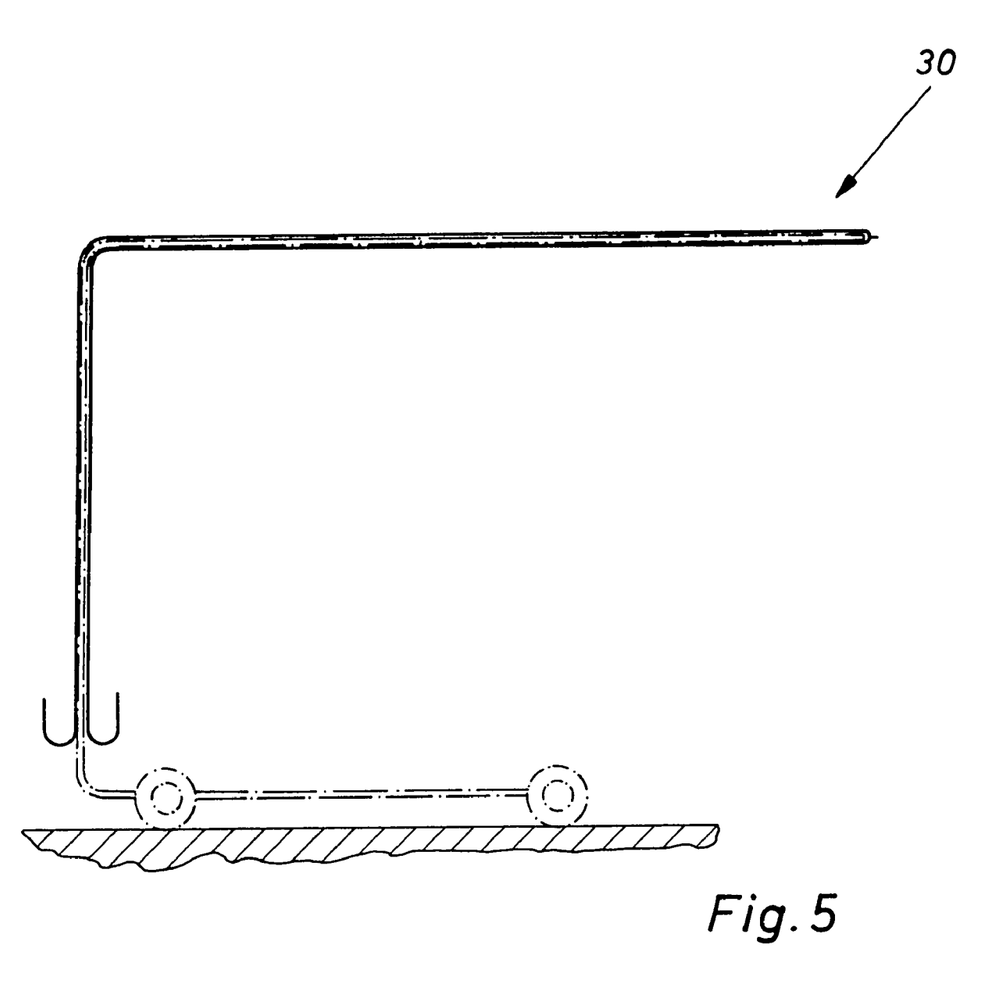
FIG. 5 schematically shows a cover, which has been completely drawn onto an instrument table.

FIG. 4 shows the cover 30 in the state where it is further pulled onto the instrument table 2. The reversely drawn or folded intermediate sections 46, 48 automatically unfold without any disturbing resistance during handling when the free table end 24 abuts the inside of the second closed end 34 which forms a stop 53. The unfolding ends 50, 52 move in the pulling direction 16 of FIGS. 3, 4 towards the left until the intermediate sections 46, 48 are completely unfolded and the table cover assumes its completely unfolded tubular shape (FIG. 5).

It is clear that several intermediate sections can be reversely drawn or folded in the inventive fashion.

In the inventive embodiment of FIGS. 3 and 4, the edge section 54, provided at the first open end 32, is outwardly folded about the periphery, i.e. above and below the folding plane, to form a handling aid 56. The peripheral folding of the edge section 54 retains the cover 30 in the folded configuration which is particularly advantageous for handling, to be able to push the cover onto the free end of an instrument table or operation table without producing disadvantageous unfolding of the cover.

FIGS. 6 through 10 schematically illustrate the reverse drawing of the intermediate section 46, 48 into the inside of the tubular web section 36. A tubular web section 36 extending in the longitudinal direction 16 and having two open ends 32, 34 is drawn onto a first cylindrical tubular body 60 along a first length $L_R$ such that it projects with a remaining length $(L-L_R)$ (not shown) past an end 62 of the tubular body 60. The projecting part of the tubular web section 36 is then inserted through or into a second tubular body 64 having a slightly smaller outer diameter than the inner diameter of the first tubular body 60 for insertion into the first tubular body 60. The second tubular body 64 is then inserted into the first tubular body 60 and carries along the projecting part of the web section 36 to reversely draw the intermediate section 46, 48 into the tubular structure. An end 66 of the second tubular body 64 pushed into the first tubular body 60 thereby forms the unfolding ends 50, 52 of the reversely drawn intermediate section 46, 48 shown in FIGS. 3 and 4 which then have a circular shape corresponding to the circular opening of the second tubular body 64.

Figure 7:
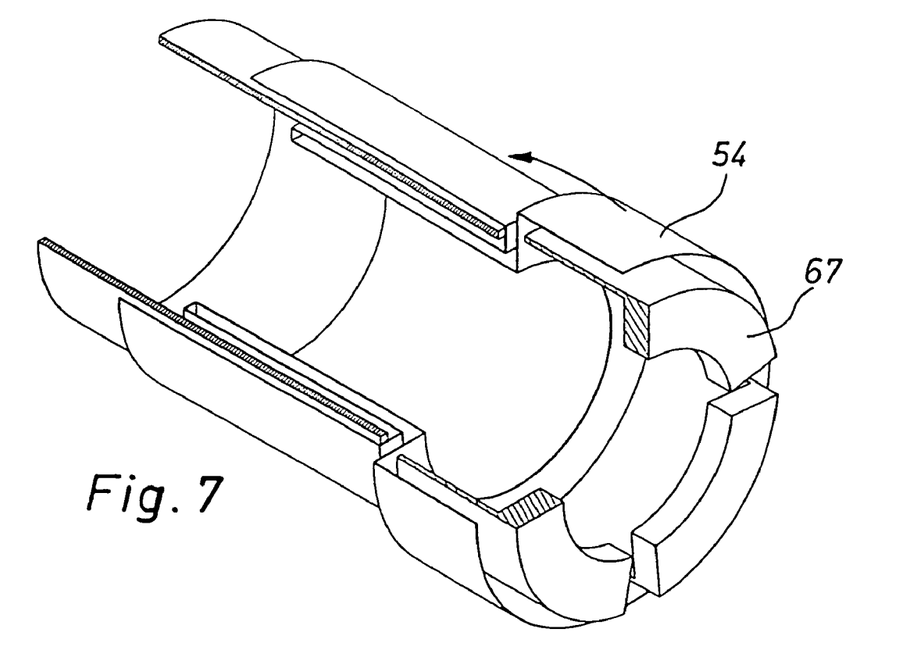
FIG. 7 shows the device of FIG. 6 in a second folding stage.
Figures 8, 9, 10:
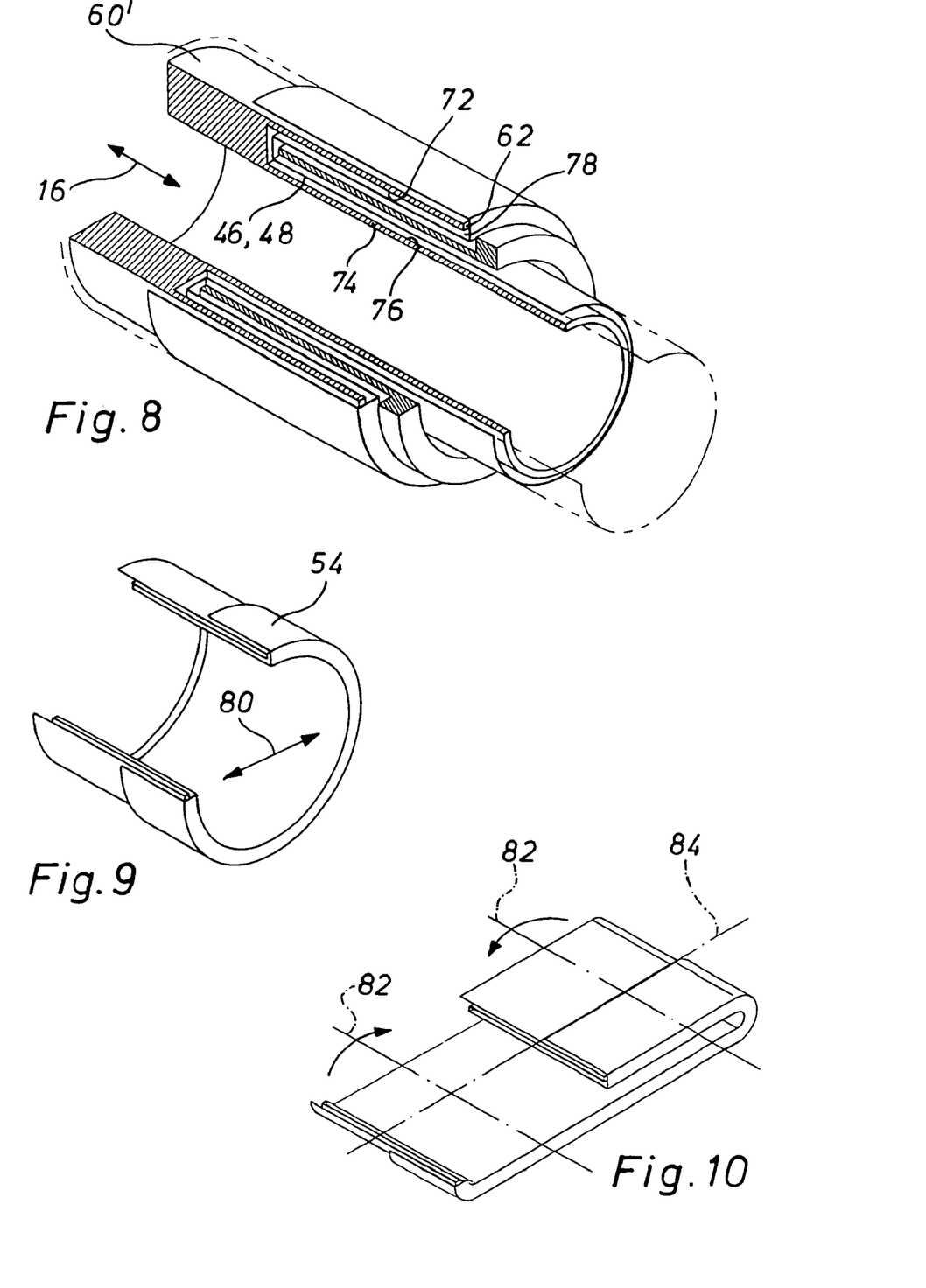
FIG. 8 shows a second device for folding the cover.
FIG. 9 shows the folded cover.
FIG. 10 shows the cover of FIG. 9 in a flat configuration.

When the second tubular body 64 has been removed from the first tubular body 60 in the opposite longitudinal direction 16, an edge section 54 (see FIG. 7) can be outwardly folded into the configuration of FIG. 9 using e.g. radially movable segments 67 (see FIGS. 6 and 7) which can also be displaceable in the longitudinal direction 16 for folding the edge section 54.

Figure 6:
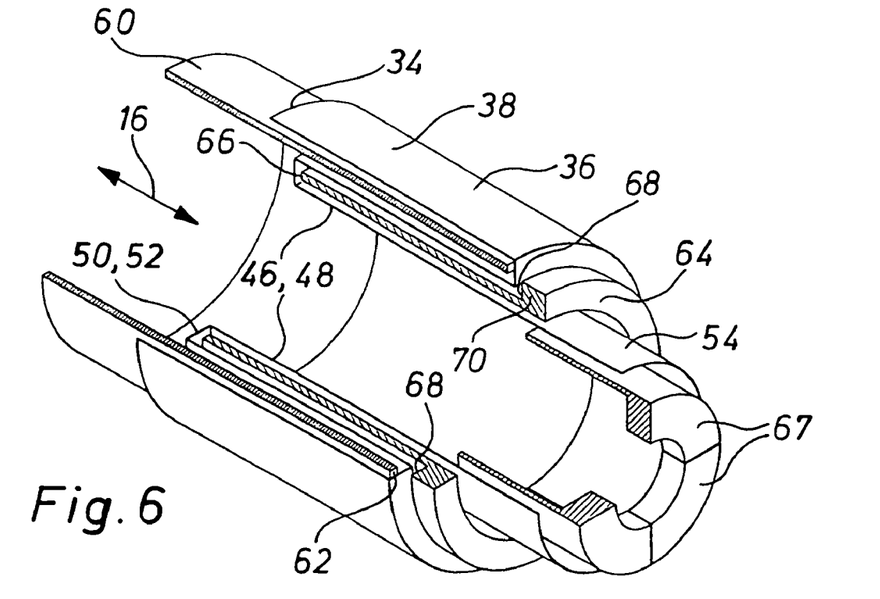
FIG. 6 shows a first device for folding the cover in a first folding stage.

As shown in FIGS. 6 and 7, the inserting motion of the second tubular body 64 into the first tubular body 60 is delimited by an end stop 68, which is formed by a radially outwardly extending annular collar 70 on the second tubular body 64. When the second tubular body is inserted, the annular collar 70 abuts the end 62 of the first tubular body 60 thereby forming a defined insertion length.

FIG. 8 shows an alternatively designed first tubular body 60' having a recess 72 which is cylindrically concentric to the longitudinal axis 16 having an end 62 and into which the second tubular body 64 can be inserted in the longitudinal direction 16 while carrying along the intermediate section 46, 48. This cylindrical recess 72 is radially delimited in an inward direction by an inner wall section 74 of the first tubular body 60'. This wall section 74 forms a guiding means 76 for the second tubular body 64 and mainly for the intermediate section 46, 48 that is reversely drawn into the cylindrical recess 72 by the second tubular body 64. As seen in FIG. 8, the wall section 74 preferably extends in the longitudinal direction 16 past the end 62 of the radially outer wall of the first tubular body 60' such that a region 78 of the tubular web section 36 is advantageously guided and disposed in a well-defined manner at that location.

When all tubular bodies 60, 64 have been removed, the folded configuration of FIG. 9 can be displaced into a substantially flat configuration (shown in FIGS. 3 and 4 in sectional view and in FIG. 10 in perspective view) through a direction 80 transverse to the longitudinal direction 16. This flatly folded configuration could e.g. be further folded about longitudinal or transverse axes 82, 84 (see FIG. 10) or can be optionally rolled for transport or storage.

Figure 11:
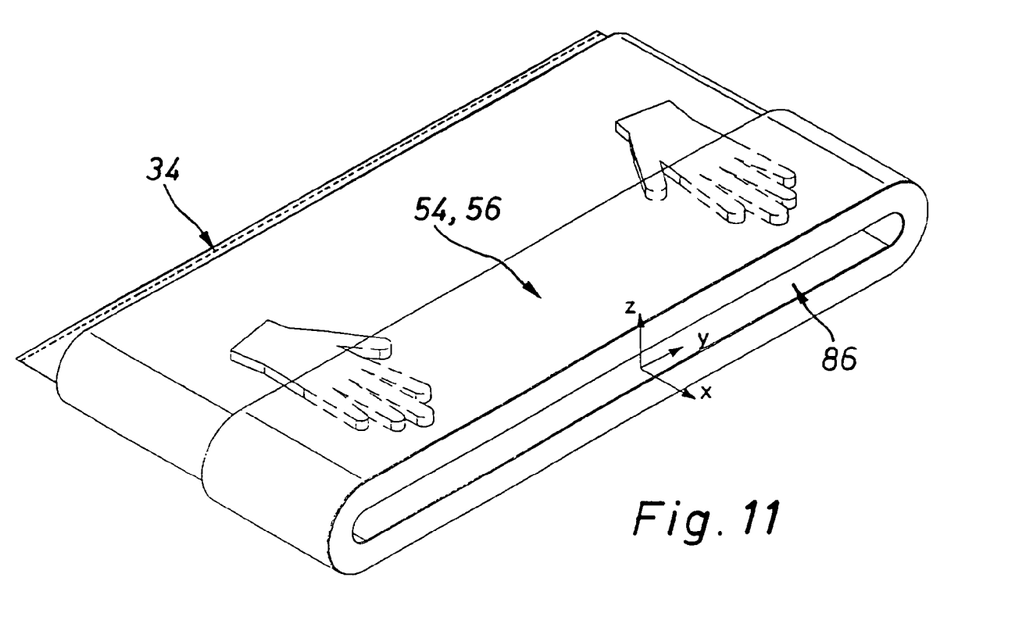
FIG. 11 schematically shows the cover folded in a flat configuration in accordance with FIGS. 6 through 10.

FIG. 11 shows a schematic perspective view of the cover folded into a flat configuration. The closed second end 34 is formed by a liquid-tight bottom seam and the folded edge section 54 forms a grasping aid 56. The illustrated hands suggest proper engagement, with a flat hand disposed below the folded edge section 54. The inventive single opening 86 for pulling over a table or an extremity of a patient is also indicated.

We claim:
1. A folded medical instrument table cover made from a tubular web section, the cover for use in an operation room, the cover comprising:
   a first open end for pulling the cover onto the instrument table;
   a second closed end forming a stop for pulling the cover onto the instrument table;
   a handling aid disposed at a vicinity of said first open end for manually grasping the cover with a user's hand for pulling the cover onto the table, said handling aid consisting essentially of an edge section of the cover outwardly folded over at said open end to form a fold for engagement by the user's hand; and
   an intermediate section disposed, in a longitudinal direction, between said second end and said first open end, said intermediate section being reversely drawn inwardly into the tubular web section such that the table can be inserted into an opening formed by said reversely drawn intermediate section, wherein said reversely drawn intermediate section can be unfolded when the cover is pulled onto the table the table abuts said second end while the cover is being applied.

2. The cover of claim 1, wherein said edge section is folded about a periphery to hold the folded cover in a flatly folded configuration.

3. The cover of claim 1, wherein said edge section has a longitudinal extent of approximately 0.2 to 0.5 a length of the folded cover.

4. The cover of claim 1, wherein said intermediate section comprises a plurality of subsections disposed between said second end and said first open end which are reversely drawn inwardly into the tubular web section.

5. The cover of claim 1, wherein an unfolding end of said reversely drawn intermediate section formed by reverse drawing into the tubular web section is proximate said stop at said second end of the cover.

6. The cover of claim 1, further comprising an absorbing surface disposed on at least one side of the cover.

7. The cover of claim 6, wherein said absorbing surface comprises a fleece material base.

* * * * *